US00PP10368P

United States Patent [19]

Deroose

[11] Patent Number: Plant 10,368

[45] Date of Patent: Apr. 28, 1998

[54] VRIESEA PLANT NAMED 'CHARLOTTE'

[76] Inventor: Reginald Deroose, Droogte 139, B-9940 Evergem, Belgium

[21] Appl. No.: 668,626

[22] Filed: Jun. 19, 1996

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 8,657 3/1994 Hill, Jr. ..... Plt./88.8

P.P. 9,410 12/1995 DeRoose et al. ..... Plt./88.8

P.P. 9,678 10/1996 Hill, Jr. ..... Plt./88.8

*Primary Examiner*—Howard J. Locker

*Assistant Examiner*—Kent L. Bell

*Attorney, Agent, or Firm*—Foley & Lardner

[57] ABSTRACT

A new and distinct cultivar of Vriesea plant named 'Charlotte', characterized by its bright yellow inflorescence, with each bract being infused with red at its base, five to eight branches each of which is about 10 cm in length, 30 to 40 cm total bract height, and its abundant dark green foliage.

1 Drawing Sheet

The present invention comprises a new and distinct cultivar of Vriesea plant, referred to by the cultivar name 'Charlotte'. The genus Vriesea is of the family Bromeliaceae.

'Charlotte' is a product of a planned breeding program conducted in Evergem, Belgium and was originated from a cross between Vriesea 'Marjan' (male or pollen parent) and Vriesea 'Marjolein' (female or seed parent), performed by the inventor Reginald Deroose.

'Charlotte' was discovered and selected within the progeny of the stated cross by Reginald Deroose in 1987 in a controlled environment in Evergem, Belgium. Subsequent asexual reproduction of 'Charlotte' by tissue culture performed by Reginald Deroose in Evergrem has demonstrated that the combination of characteristics as herein disclosed for 'Charlotte' are firmly fixed and retained through successive generations of asexual reproduction.

'Charlotte' has not been observed under all possible environmental conditions. The phenotype may vary significantly when grown under different conditions of temperature, light, and other determining factors, without, however, any variation in the genotype. The following observations, measurements and comparisons describe plants grown in Evergem, Belgium, under greenhouse conditions which closely approximate those generally used in horticultural practice.

The following traits have been repeatedly observed and are determined to be basic characteristics of 'Charlotte' which in combination distinguish this Vriesea as a new and distinct cultivar:

1. The inflorescence is bright yellow with a small amount of red at the base of each bract, is about 30 cm to 40 cm in total height.

2. Each inflorescence has about 5 to 8 branches, each about 10 cm long.

3. The branches are nearly horizontally placed on the main stem.

4. Abundant medium green foliage in a dense rosette.

The new cultivar can be compared to both of its parents. With respect to the maternal parent cultivar 'Marjan', both cultivars have similar plant shape and yellow inflorescence infused with red. However, 'Charlotte' has more and somewhat wider leaves which bend more downwardly, the inflorescence and total plant are smaller, the bracts of 'Charlotte' are more horizontal on the main stem, with the bracts of 'Marjan' being nearly vertically placed, and the leaves of 'Charlotte' are entirely green, including the lower surface. 'Marjan' has a slightly red color on the lower surface of the leaves.

With respect to 'Marjolein', the plant and flower shapes are similar. The bracts of 'Marjolein' are red in color in the middle with yellow tips, compared to the mainly yellow bracts of 'Charlotte' with a red base. The bracts of 'Marjolein' are at a 60° angle to the main stem, and the leaves are more erect.

The accompanying color photographic drawing comprises a side perspective view of a typical plant of 'Charlotte' in bloom.

In the following description, color references are made to The Royal Horticultural Society Colour Chart, except where color terms of ordinary significance are used. The color values were determined between 1:00 p.m. and 2:00 p.m. in September 1990 under bright daylight conditions.

Classification:

*Botanical.*—Vriesea cv. 'Charlotte'.

*Commercial.*—Vriesea 'Charlotte'.

Parentage:

*Male parent.*—'Marjolein'.

*Female parent.*—'Marjan'.

Propagation: Asexual propagation is preferably by tissue culture.

Plant:

*Form.*—Rosette.

*Height.*—Approximately 30 cm to 40 cm in total height including inflorescence when grown in a 11 cm pot, and about 50 cm in diameter.

*Growth habit.*—Excellent, very vigorous.

*Foliage.*—Quantity: Abundant. Size of leaf: 20 to 30 cm in length, about 6 cm wide at the widest point of the leaf. Shape of leaf: Oblong with tips bending down, rounded and apiculate. Surface texture: Glabrous. Margin: Entire. Color: Upper side 137A-147A; underside 137A. Veins: Upper surface: slightly visible. Under surface: visible. Sheaths: Broad, distinct, green, much wider than blades.

Inflorescence:

*Scape.*—Oriented erect to a little oblique, about 13 to 16 cm long and 1 cm in diameter, glabrous; 5 to 8 branches, each about 10 cm in length and 4.5 cm in width, color 14A, with the base being approximately 44A-45B. The color of the branches or bracts lasts 3 to 4 months.

*Bract shape.*—Oval.

*Bract size.*—10 cm long and 4.5 cm wide, alternately arranged.

*Number of bracts.*—5 to 8.

*Color.*—Mainly 14A, 44A-45B at the base.

*Flowers.*—In the floral bracts, one flower per bract, typical for the genus Vriesea. Flowering normally in progression from base to tip of scape or bracts, with many flowers at the same time. Flowers are transparent light yellow 12D-11D in color at the base to yellow 12A at the tip. After buds are visible, approximately 6 weeks are required for flowers to fully develop.

*Fragrance.*—None.

Reproductive organs:

*Stamens.*—1 per flower, color 2A.

*Pistils.*—6 per flower, color 17A.

Resistance to disease: No disease problems have been noted to date.

I claim:

1. A new and distinct cultivar of Vriesea plant named 'Charlotte', as illustrated and described.

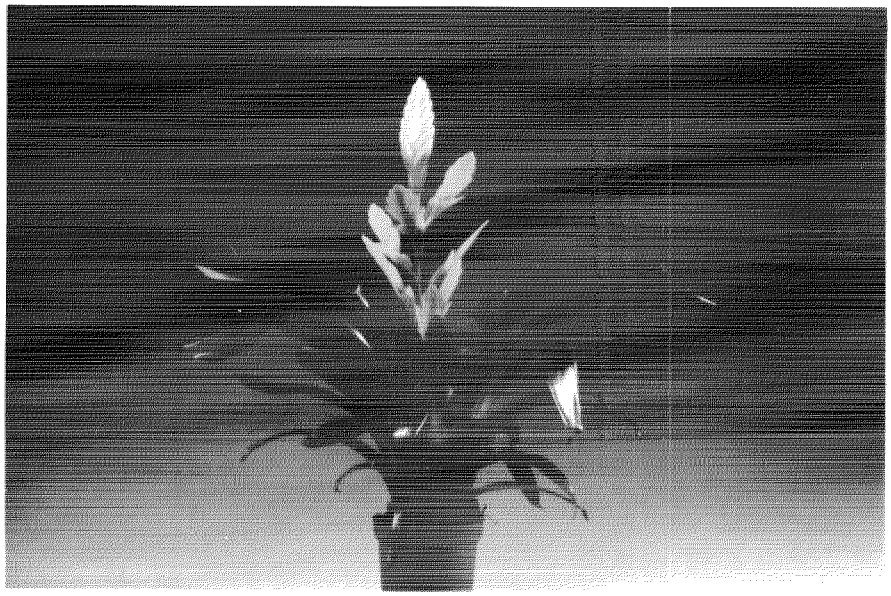

* * * * *